United States Patent [19]
Kraus et al.

[11] Patent Number: 5,883,258
[45] Date of Patent: Mar. 16, 1999

[54] PROCESS FOR PREPARING 3-CHLOROBENZISOTHIAZOLES

[75] Inventors: Helmut Kraus; Andreas Krebs, both of Odenthal; Robert Söllner, Leverkusen, all of Germany

[73] Assignee: Bayer Aktiengesellschaft, Leverkusen, Germany

[21] Appl. No.: 968,053

[22] Filed: Nov. 10, 1997

[30] Foreign Application Priority Data

Dec. 9, 1996 [DE] Germany .................. 196 51 038.4

[51] Int. Cl.⁶ .................................................. C07D 275/04
[52] U.S. Cl. ........................................................ 548/207
[58] Field of Search .............................................. 548/207

[56] References Cited

U.S. PATENT DOCUMENTS 4,590,196  5/1986  Smith et al. ............................ 514/253

FOREIGN PATENT DOCUMENTS

| 0196096 | 10/1986 | European Pat. Off. . |
|---------|---------|----------------------|
| 2029387 | 1/1971  | Germany . |
| 3530089 | 3/1986  | Germany . |
| 5024271 | 6/1973  | Japan ..................................... 548/207 |
| 704013  | 6/1970  | South Africa . |

OTHER PUBLICATIONS

P.V. Plazzi et al., Sintesi e proprietá biologiche de ell'acido 2–metil–2–[5–cicloesil–1,2–benzoistiazil–3–11]acetico, *L'Ateneo Parmense acta naturalia,* vol. 15 (1979) pp. 49–55 plus cover sheet.

Mark H. Norman et al., Synthesis of 13C–Labeled 1192U90, an Ortho–Amino Benzamide with a Preclinical Atypical Antipsychotic Profile, *Journal of Labelled Compounds and Radiopharmaceuticals,* vol. 38, No. 3, (Mar. 1996), pp. 269–280 plus cover sheet.

Kutze Originalmitteilungen: Zur Darstellung halogenierter Isothiazolium—und Isoxazoliumsalze, Z. Chem., 8, 170 (1968).

Über 3–Acylimino–3H–1.2 benzoditihiole Chem. Ber. 101, 2472–2484 (1968).

Das 3–Chlor–1.2–benzisothiazolium–Kation, Z. Naturforschung 206, 712, (1965).

*Primary Examiner*—Robert Gerstl
*Attorney, Agent, or Firm*—Sprung Kramer Schaefer & Briscoe

[57] ABSTRACT

N-Unsubstituted 3-chlorobenzisothiazoles are obtained by reacting N-unsubstituted benzisothiazolones with phosgene in the presence of catalysts.

11 Claims, No Drawings

PROCESS FOR PREPARING 3-CHLOROBENZISOTHIAZOLES

The present invention relates to a process for preparing 3-chlorobenzisothiazoles by reacting the corresponding benzisothiazolones with phosgene in the presence of a catalyst.

3-Chlorobenzisothiazoles are important intermediates for preparing pharmaceutically active compounds (see for example U.S. Pat. No. 5,206,366 and EP-A1 281 309) and crop protection agents (see for example DE-A1 20 29 387).

3-Chlorobenzisothiazoles can be prepared for example starting from 2,2'-di-carboxydiphenyl disulfides via the amides to give 3-chloro-1,2-benzisothiazolium chlorides and subsequent pyrolysis (see EP-A1 196 096).

However, it is customary to start from benzisothiazolones, some of which are commercially available, and to chlorinate them with phosphorus oxychloride (see for example DE-A1 35 30 089 and Chem. Ber. 101, 2472 (1968)). This gives the 3-chlorobenzisothiazoles in 60 to 80% yield. However, aqueous work-up is required to remove the polyphosphoric acids which are formed from phosphorus oxychloride. This requires extraction with two organic solvents, purification with activated carbon, and distillation. Owing to the phosphorus-containing waste waters which have to be disposed of and the complicated work-up, this process is costly and not economically viable.

The reaction of N-substituted benzisothiazoles with oxalyl chloride and with phosgene to give 3-chloro-1,2-benzisothiazolium chlorides in 90% yield has been described (see Z. Naturforschung 20b, 712 (1965) and Z. Chem. 8, 170 (1968)). When this process is applied to N-unsubstituted benzisothiazoles, long reaction times are required and yields are drastically reduced (see the present Comparative Example).

This invention, accordingly, provides a process for preparing N-unsubstituted 3-chlorobenzisothiazoles of the formula

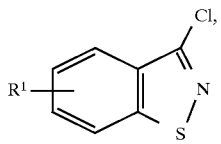

in which
R$^1$ represents hydrogen, halogen, nitro, C$_1$–C$_6$-alkyl or C$_1$–C$_6$-alkoxy, which comprises reacting N-unsubstituted benzisothiazolones of the formula

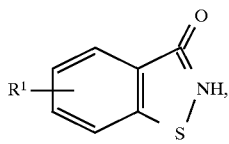

in which
R$^1$ is as defined for formula (I),
with phosgene in the presence of catalysts of the formula (III)

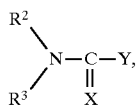

in which
R$^2$ and R$^3$ independently of one another each represent C$_1$–C$_6$-alkyl or C$_5$–C$_7$-cycloalkyl, X represents oxygen or NH and
Y represents hydrogen or a radical of the formula

in which
R$^4$ and R$^5$ independently of one another each represent C$_1$–C$_6$-alkyl or C$_5$–C$_7$-cycloalkyl,
where Y in the case of X=NH only represents a radical of the formula (IV) and
where R$^4$ and R$^5$ together in the case of X=oxygen and Y=a radical of the formula (IV) also represent
a) —(CHR$^6$)$_n$—where n=an integer from 2 to 4,
b) —CHR$^6$—O—CHR$^6$—or
c) 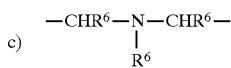

where each R$^6$ independently of the others may represent hydrogen, C$_1$–C$_6$-alkyl or C$_5$–C$_7$-cycloalkyl.

Halogen represents, for example, fluorine, chlorine or bromine.

C$_1$–C$_6$-Alkyl represents, for example, methyl, ethyl, n-propyl, i-propyl, n-butyl, i-butyl, sec-butyl, tert-butyl, amyl or hexyl. Preference is given to methyl, ethyl, n-propyl, i-propyl, n-butyl, i-butyl, sec-butyl, tert-butyl.

C$_1$–C$_6$-Alkoxy may, for example and preferably, contain an alkyl moiety as illustrated immediately above for the C$_1$–C$_6$-alkyl radicals.

C$_5$–C$_7$-Cycloalkyl represents, for example, cyclopentyl, cyclohexyl or cycloheptyl.

Preferred benzisothiazolones of the formula (II) are unsubstituted benzthiazolone and N-unsubstituted benzthiazolones in which R$^1$ represents chlorine.

Preferred catalysts of the formula (III) are those in which
a) X represents oxygen and Y represents hydrogen and R$^2$ and R$^3$ are identical and each represents C$_1$–C$_4$-alkyl,
b) X represents oxygen or NH and Y represents a radical of the formula (IV) where R$^2$ to R$^5$ are identical and each represents methyl or ethyl and
c) X represents oxygen and Y represents a radical of the formula (IV) where R$^2$ and R$^3$ are identical and each represents C$_1$–C$_4$-alkyl and R$^4$ and R$^5$ together represent—(CH$_2$)$_2$—or—(CH$_2$)$_3$—.

According to the invention, preference is given to preparing 3-chlorobenzisothiazoles of the formula (I) in which R$^1$ represents hydrogen or chlorine.

Owing to the high melting point of the benzisothiazolones of the formula (II), the process according to the invention is preferably carried out in diluents. Suitable diluents are, for example, toluene, xylenes, isopropylbenzenes, chlorobenzene, di-chlorobenzenes, diphenyl, methylcyclohexane and higher aliphatic hydrocarbons such as, for example, octane, nonane and decane. It is also possible to use mixtures of these solvents.

If only benzisothiazolones of the formula (II) containing residual water are available, it is advantageous to remove this water prior to carrying out the process according to the invention, for example by azeotropic distillation, where the preferred auxiliary for the azeotropic distillation is the diluent intended for the reaction, for example a chlorinated aromatic compound.

The process according to the invention can be carried out at reaction temperatures of, for example, from 50° to 150° C. The reaction temperature is preferably from 80° to 130° C.

The catalyst of the formula (III) can be employed for example in an amount of from 0.5 to 200 mol %, based on the benzisothiazolone of the formula (II) employed. This amount is preferably from 0.7 to 100 mol %, particularly preferably from 1 to 20 mol %.

Phosgene is preferably employed in excess. For example, 1.2 to 10 mol of phosgene can be used per mole of benzisothiazolone of the formula (II). This amount is preferably from 1.3 to 5 mol, in particular from 1.4 to 3 mol. It is also possible to introduce phosgene until no more is taken up by the reaction mixture.

The process according to the invention is preferably carried out by initially charging the starting material, the catalyst and, if appropriate, the diluent and introducing phosgene at the desired reaction temperature.

Excess phosgene and other escaping reaction gases can be drained off over an activated carbon tower which is trickled with water. However, preference is given to condensing the major part of the escaping phosgene in a low-temperature condenser, for example at −15° to −75° C. This phosgene may then, if required after appropriate purification, be used once more for phosgenation reactions, for example also in the process according to the invention.

After the introduction of phosgene has ended, it is advantageous to continue stirring at the reaction temperature or any other temperature in the range from 50° to 150° C. for some time, for example until virtually no more gases are formed.

For work-up of the reaction mixture, initially any phosgene that may still be present can be removed, for example by passing nitrogen through the reaction mixture. If appropriate, the solvent can then be distilled off under atmospheric pressure or under slightly reduced pressure, and the residue can subsequently be subjected to a vacuum distillation. In this manner, it is generally possible to obtain 3-chlorobenzisothiazole of the formula (I) of a purity of more than 98% in yields of up to more than 90% of theory (after the distillation).

The advantages that can be achieved by preparing N-unsubstituted chloro-benzisothiazoles according to the invention are extremely surprising since this reaction does not proceed analogously to the corresponding reactions for preparing N-substituted chlorobenzisothiazoles and the known processes for preparing N-substituted chlorobenzisothiazoles cannot be applied to the preparation of N-unsubstituted chlorobenzthiazoles.

EXAMPLES

Example 1

565 g of benzisothiazolone (content: 92.8% by weight; volatile components: 28.05% by weight; total effective content: 66.8% by weight =2.5 mol) were admixed with 500 ml of chlorobenzene and any water present was removed azeotropically. About 150 ml of water were separated off, and the distilled chlorobenzene was recycled.

After the addition of 20.2 g of tetramethylguanidine, 400 g of phosgene were introduced at 120° C. Subsequently, nitrogen was passed through the reaction mixture for 2 hours and the solvent was then distilled off under atmospheric pressure at a bottom temperature of 150° C. Vacuum distillation (130° C./10 mbar) gave 373 g of 98% pure 3-chlorobenzisothiazole (=86.3% of theory).

Example 2

Similarly to Example 1, 406 g of dry, 93% pure benzisothiazolone with 20.3 g of tetramethylurea were phosgenated in o-chlorobenzene. Vacuum distillation gave 3-chlorobenzisothiazole in a yield of 84.9% of theory.

Example 3

Example 2 was repeated, except that 28 g of dibutylformamide and 600 ml of nonane were used as catalyst and as solvent, respectively. 3-Chlorobenzisothiazole was obtained in a yield of 78.8% of theory.

Example 4

190 g of dry, 97.7% by weight pure benzisothiazolone were initially charged in 500 ml of chlorobenzene. 5.1 g of 1,3-dimethyltetrahydro-2-(1H)-pyrimidinone were then added, the reaction mixture was heated to 120° C. and about 250 g of phosgene were introduced over a period of 5 hours. Most of the gases leaving the reactor were condensed in a condenser which was operated with a cooling agent of −25° C.

The reaction mixture was dephosgenated by passing nitrogen through the reaction mixture for 2 hours, and then first chlorobenzene was distilled off under atmospheric pressure and then 3-chlorobenzisothiazole under reduced pressure. The yield was 85.6% of theory.

Example 5

Example 4 was repeated, except that 4.5 g of 1,3-dimethylimidazolidinone were used as catalyst. Vacuum distillation gave 3-chlorobenzisothiazole in a yield of 89.3% of theory.

Example 6

Example 5 was repeated, except that 4 kg of 93% by weight pure benzisothiazolone and 90 g of 1,3-dimethylimidazolidinone in 5 l of chlorobenzene were phosgenated. To obtain the reaction product, 200 ml of high boiling paraffin oil were added prior to the vacuum distillation, and a Vigreux column of 20 cm in length was used. 3-Chlorobenzisothiazole of a purity of 99.4% by weight was obtained in a yield of 92.7% of theory.

Example 7 (for comparison)

(By the method of Z. Naturforsch. 20b, 712 (1965) and Z. Chem. 8, 170 (1968))

190 g of dry, 97.7% by weight pure benzisothiazolone were phosgenated in 500 ml of xylene at 130° C. without addition of a catalyst for 24 hours. Examination of the resulting reaction mixture by HPLC showed that the solution contained 3-chlorobenzisothiazole in an amount corresponding to a yield of 16.3% of theory. In addition, the solution contained 38.8% by weight of the benzisothiazole used as starting material.

What is claimed is:

1. A process for preparing an N-unsubstituted 3-chlorobenzisothiazole of the formula

in which $R^1$ represents hydrogen, halogen, nitro, $C_1$–$C_6$-alkyl or $C_1$–$C_6$-alkoxy, which comprises reacting an N-unsubstituted benzisothiazolone of the formula

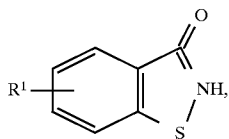   (II)

in which $R^1$ is as defined for formula (I), with phosgene in the presence of a catalyst of the formula (III)

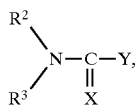   (III)

in which $R^2$ and $R^3$ independently of one another each represent $C_1$–$C_6$-alkyl or $C_5$–$C_7$-cycloalkyl, X represents oxygen or NH and Y represents a radical of the formula

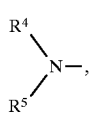   (IV)

in which $R^4$ and $R^5$ independently of one another each represent $C_1$–$C_6$-alkyl or $C_5$–$C_7$-cycloalkyl, where Y in the case of X=NH only represents a radical of the formula (IV) and where $R^4$ and $R^5$ together in the case of X=oxygen and Y=a radical of the formula (IV) also represent a) —(CHR$^6$)$_n$— where n=an integer from 2 to 4, b) —CHR$^6$—O—CHR$^6$— or c) 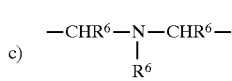

where each $R^6$ independently of the others may represent hydrogen, $C_1$–$C_6$-alkyl or $C_5$–$C_7$-cycloalkyl.

2. The process as claimed in claim 1, wherein in the formulae halogen represents fluorine, chlorine or bromine, $C_1$–$C_6$-alkyl represents methyl, ethyl, n-propyl, i-propyl, n-butyl, i-butyl, sec-butyl, tert-butyl, amyl or hexyl, $C_1$–$C_6$-alkoxy represents methoxy, ethoxy, n-propoxy, i-propoxy, n-butoxy, i-butoxy, sec-butoxy, tert-butoxy, amyloxy or hexyloxy and $C_1$–$C_7$-cycloalkyl represents cyclopentyl, cyclohexyl or cycloheptyl.

3. The process as claimed in claim 1, wherein a benzisothiazolone of the formula (II) is employed in which $R^1$ represents hydrogen or chlorine.

4. The process as claimed in claim 1, wherein a catalysts of the formula (III) is employed in which a) X represents oxygen and Y represents hydrogen and $R^2$ and $R^3$ are identical and each represents $C_1$–$C_4$-alkyl, b) X represents oxygen or NH and Y represents a radical of the formula (IV) where $R^2$ to $R^5$ are identical and each represents methyl or ethyl or c) X represents oxygen and Y represents a radical of the formula (IV) where $R^2$ and $R^3$ are identical and each represents $C_1$–$C_4$-alkyl and $R^4$ and $R^5$ together represent —(CH$_2$)$_2$— or —(CH$_2$)$_3$—.

5. The process as claimed in claim 1, wherein said process is carried out in the presence of a diluent.

6. The process as claimed in claim 1, wherein said process is carried out at reaction temperatures of from 50° to 150° C.

7. The process as claimed in claim 1, wherein the catalyst of the formula (III) is employed in an amount corresponding to 0.5 to 200 mol %, based on the benzisothiazolone of the formula (II) employed.

8. The process as claimed in claim 1, wherein 1.2 to 10 mol of phosgene are employed per mole of benzisothiazolone of the formula (II).

9. The process as claimed in claim 1, wherein the starting material and the catalyst are initially charged and phosgene is introduced at the desired reaction temperature.

10. The process as claimed in claim 1, wherein the starting material, the catalyst and a diluent are initially charged and phosgene is introduced at the desired reaction temperature.

11. The process as claimed in claim 1, wherein the reaction mixture is stirred until virtually no more gases are formed at the reaction temperature or any other temperature in the range from 50° to 150° C. after the phosgene uptake has ended, excess phosgene is then removed, the diluent, if present, is subsequently removed under atmospheric pressure or under slightly reduced pressure and the reaction product is obtained by vacuum distillation.

* * * * *